United States Patent [19]

Viertl et al.

[11] Patent Number: 5,329,230

[45] Date of Patent: Jul. 12, 1994

[54] CARRIAGE FOR EDDY CURRENT PROBE HAVING CONTACT BALL ENGAGEMENT BETWEEN CARRIAGE AND TRANSLATION MEANS

[75] Inventors: John R. M. Viertl, Niskayuna, N.Y.; Fred R. Burkhardt, Jr., Chesterfield, Va.

[73] Assignee: General Electric Company, Schenectady, N.Y.

[21] Appl. No.: 729,725

[22] Filed: Jul. 15, 1991

[51] Int. Cl.⁵ .................. G01N 27/72; G01R 33/12
[52] U.S. Cl. .................... 324/262; 324/226; 324/238
[58] Field of Search ............ 324/225, 262, 243, 242, 324/241, 233, 238, 237, 226

[56] References Cited

U.S. PATENT DOCUMENTS 4,134,067  1/1979  Woodbury ................ 324/241
4,258,319  3/1981  Shimada et al. ............ 324/262

Primary Examiner—W. Snow
Attorney, Agent, or Firm—Nixon & Vanderhye

[57] ABSTRACT

An eddy current probe for detecting material flaws by inducing and measuring eddy currents in the surface of a material. The probe is held at a constant lift-off distance from the surface by a probe carriage that slides across the surface in a straight scan line. The carriage moves relative to a motorized bracket that slides the carriage across the surface. This relative movement allows the carriage to move across an uneven surface without deflecting the probe from a straight scan line. The probe has a split core so that an adjacent pair of coils project and detect electromagnetic fields on the surface being measured. Both coils have opposing flat sides that allow the coils to be closely packed together within the probe body.

5 Claims, 5 Drawing Sheets

CARRIAGE FOR EDDY CURRENT PROBE HAVING CONTACT BALL ENGAGEMENT BETWEEN CARRIAGE AND TRANSLATION MEANS

FIELD OF THE INVENTION

This application relates to eddy current probes for detecting flaws in conductive materials or semiconductive materials and, in particular, to eddy current probes for detecting flaws in retaining rings for electromagnetic generators.

BACKGROUND AND SUMMARY OF THE INVENTION

Eddy currents provide a measurable parameter indicative of flaws in the surface and sub-surface of materials. Eddy currents are generally confined to the surface and near surface regions of the material. Eddy currents are affected by changes in the resistivity of the material. Flaws in the material, such as microscopic hair line cracks or pits, affect the localized resistivity of the material. Flaws in a material cause localized variations in the eddy currents in the material. Accordingly, a material can be inspected for flaws by inducing and measuring eddy currents in the material.

Eddy current probes detect material flaws by sensing variations in eddy currents. These probes have coils with high frequency currents that project a fluctuating magnetic field into the conductive material being measured. This imposed magnetic field induces eddy currents in the material. The strength of the eddy currents depends on the local resistivity of the material which is affected by the presence of material flaws. These eddy currents create a magnetic field that varies in intensity with the strength of the eddy current and, hence, the presence of material flaws.

The magnetic field created by the eddy currents extends above the material surface to the probe. Thus, the magnetic field from the eddy current induces its own voltage in the probe coil. The eddy magnetic field opposes the coil field. These coupled magnetic fields measurably affect the net current and inductance of the probe coils. These variations in the coil currents vary in response to material flaws and, thus, are measured to detect these flaws.

For the probe coil current to reliably indicate variations in eddy currents, other parameters that affect the coil current must be constant. One such parameter is the distance between the face of the probe and the surface of the material. The degree of coupling between the magnetic fields from the coil current and the eddy current depends on the gap between the probe and the material with the eddy currents. The gap between the probe and material is known in the art as being the "lift-off" of the probe. Prior probes do not have a reliably constant lift-off. Lift-off has long-posed difficulties to eddy current probes that have not been solved until now.

Changes in the lift-off gap alter the amount of magnetic coupling and, hence, the coil current. The eddy current probe detects current alterations due to gap changes just as it detects variations in the eddy current due to material flaws. Since it is desired to detect only eddy current alterations due to material flaws, variations due to changes in the lift-off gap must be prevented. Accordingly, the gap between the probe and the material surface must be held constant to ensure proper operation of the probe.

It is difficult to maintain a constant distance between the probe and the material being-tested. It is particularly difficult to maintain a constant gap when a large surface, such as a retaining ring for a power generator, is being tested. These retaining rings are large and typically have radii in the range of 13 to 36 inches. Because they are so large and their surfaces may have been reworked from earlier service, retaining rings are not perfect cylinders. The surface of a retaining ring is immense compared to the small material flaws that an eddy current probe is to detect. There are small irregularities in the shape of the retaining ring that deform the ring from a true cylinder. Similarly, large retaining rings do not have surfaces that are uniform at the small order of magnitude (microcracks) at which the eddy currents are being measured. The irregularities in the shape and surface of the retaining ring have made it difficult to hold the probe at a constant distance from the surface of the ring.

Eddy current probes are usually fixed with respect to a reference other than the retaining ring. A true and known reference is necessary to precisely position the probe with respect to the retaining ring. The retaining ring usually bears a stamp on its end surface marking the zero degree position of the ring. The position of the eddy current probe is referenced from this zero reference stamp. A fixed reference for the probe is established with a conventional reference frame. This reference frame is attached to the retaining ring and is centered on the axis of the ring as is shown in FIG. 1. The eddy current probe is affixed to the reference frame and positioned near the surface of the retaining ring. The reference frame is motorized so that the eddy current probe can be drawn across the surface of the retaining ring. Generally, the probe is moved axially along the length of the retaining ring in a straight scan line.

As the probe completely traverses each scan line across the retaining ring surface, the probe is radially indexed to the next scan line around the reference frame. The probe is then drawn along this next scan line. This scanning and indexing sequence is repeated until the probe has completed scans around the entire circumference of the retaining ring. In this way, the probe covers the entire surface of the retaining ring. The probe must cover the entire ring to ensure that all material flaws are detected. To do this, the probe must travel along straight scan lines. If the probe wanders off a scan line, then portions of the material surface will be missed by the probe and flaws in the material may escape detection.

Prior to the present invention, probes have either hovered over the surface of the ring or been biased against the surface of the ring. Probes that hovered over the ring surface were held solely by the reference frame and were not directly in contact with the retaining ring. It is exceedingly difficult to maintain a constant lift-off gap between a hovering probe and the ring surface because of the irregularities in the shape and surface of the retaining ring. To maintain a constant gap between the probe and ring, other probes are pressed against the surface of the ring by the reference frame. The gap between the probe and ring surface is held constant because the probe slides directly on the surface. However, these probes rub against the surface, wear out quickly and collect dirt in the face of the probe. This rubbing also creates vibration in the probe which affects the coil current being measured. The mechanical vibration from the probe creates signal noise within the measured coil current. This noise tends to obscure the desired eddy current signals. Accordingly, until the present invention, a real need existed for an eddy current probe that did not rub against a surface, was held a constant distance from the surface of the ring and was positioned in a fixed reference frame.

In the present invention, a carriage carries the eddy current probe a fixed distance above the retaining ring surface. The carriage has self-lubricating feet that slide on the ring surface. The feet are close enough together so that large scale irregularities in the shape of the ring do not vary the gap between probe and retaining ring surface. The feet of the carriage are far enough apart so that small surface defects do not jolt or otherwise disturb the probe. In addition, this carriage can be slid across a material surface at a much-faster speed than can conventional eddy current probes.

The carriage is moved in a straight line along the surface of the retaining ring. A conventional motorized reference frame having shafts parallel to the ring axis and to the path of the carriage carries the carriage across the surface of the ring. The carriage is coupled to these shafts by a rod extending perpendicularly from the carriage. The rod is attached to the reference frame and the carriage. There are limited degrees of freedom of movement between the carriage and the rod to allow the carriage to ride on an irregular surface. However, the carriage is not permitted to move in any direction that would divert the eddy current probe from its intended straight scan line. Accordingly, as the carriage moves across the surface of the retaining ring, the eddy current probe is held to a predetermined straight scan line. This straight line movement allows the entire surface of a material be traversed without missing portions of the surface due to a wandering probe.

Some signal noise will always be present in the coil current. It is not practical to mechanically eliminate all of the sources of signal noise. Accordingly, signal processing techniques are used in the present invention to discriminate the current signals attributable to variations in the eddy current from noise and other undesirable signals. The principal signal processing technique employed in the present invention is to compare two coil signals that are nearly identical but for the desired eddy current signal. A new split coil eddy current probe provides these two similar current signals. This new probe is superior to prior differential probes such as is described in U.S. Pat. No. 4,855,677.

The present split coil probe has two separate but identical coils positioned side-by-side on the face of the probe. Unlike conventional cylindrical differential coils, the present coils have "D" shapes that allow them to be more closely packed together within the probe. This close packing of coils improves the spatial resolution of the probe because its electrical radius is smaller than that of conventional cylindrical differential coils.

Both coils have the same drive current and are drawn along adjacent parallel paths over the surface of the retaining ring. Both coils are magnetically coupled to the eddy currents they each separately induce in the retaining ring. The gap between the ring surface and the probe is the same for both coils. Accordingly, the coil currents for each coil is substantially the same.

The two coils are far enough apart so that they will not pass over the same material flaws in the ring surface at the same time. Although the coils are side by side and very close together, they do not project overlapping magnetic fields onto the same portion of the ring surface. The magnetic fields generated by the each of coils and projected against the ring surface has a shape substantially the same as the "D" shaped end of the coil. The side-by-side coils project side by side magnetic fields onto the ring surface. The opposing "D" shapes of the coils allows the projected magnetic fields to abut against one another without overlapping.

Since the flaws in the retaining ring material tend to be microscopic, individual flaws generally do not traverse across the side-by-side magnetic fields. When one probe coil passes over a material flaw, the other coil does not pass over the same flaw. Since material flaws affect the eddy currents that magnetically couple a coil, the current in the coil passing over the flaw is affected by the altered eddy current while the other coil current is not affected by the flaw. Accordingly, the difference between the two coil current signals is due to microflaws in the ring surface and sub-surface.

In addition, most of the noise and other signal effects in the eddy current probe can be masked from the coil signal by using impedance bridge and amplifier circuits to process the coil current signals. These circuits are contained in a conventional eddy current instrument such as an MIZ-40 model instrument manufactured by the Zetec Corp. of Issaquah, Wash. To further refine the signals from the eddy current probe, the coil signals from the bridge circuit are passed through two synchronous differential amplifier circuits to create two difference signals. One amplifier is synchronized with the drive oscillator. The in-phase signal, after the addition of a user selectable display phase angle ($\phi$), can be rotated on the display screen so that it generally corresponds to liftoff variations between the two coils (to the extent that such variations exist with side-by-side coils) and other noise.

The second synchronous differential amplifier has a 90° phase shift with the drive oscillator and, thus, compares the out-of-phase differences between the coil signals. The out-of-phase signal, after the addition of the same user selectable display phase angle ($\phi$), can be rotated on the display so that it generally corresponds to variations in the eddy currents between the two coils and which are due to material flaws. Since the eddy currents are generated by and magnetically coupled to the coil current, the eddy currents are slightly behind the phase of the coil current. The eddy currents tend to retard the coil current because of the magnetic coupling. Thus, the currents in the two coils will be out-of-phase due to the eddy currents.

The processed signal data from the eddy current probe is displayed via conventional display means. Strip charts have been used to show each scan line of the probe and show where the eddy current varies with respect to the material surface. Similarly, CRT display screens can be used to present the eddy current data. The display may be adjusted to show the in-phase and out-of-phase differential signals on respective horizontal and vertical display axes to enhance the user's ability to analyze the data. In addition, a computer can be used to display the signals, and to color-code and plot the signals for a display or to print a paper copy of the data. The displays have in common the presentation of data indicative of material flaws in the ring. The data may be presented such that the location of the flaws in the material is apparent or may be presented such that the area and extent of the flaws are apparent.

It is an object of the present invention to provide an improved eddy current probe, carriage and signal processor. The probe has split coils that enable the signal processor to reliably identify the eddy current variations indicative of defects in the material being scanned. The carriage maintains a constant lift-off gap between the probe and the surface of the material. The carriage also keeps the probe on a straight scan line while adjusting to variations in the surface of the material.

DETAILED DESCRIPTION OF THE DRAWINGS

Figure 1:
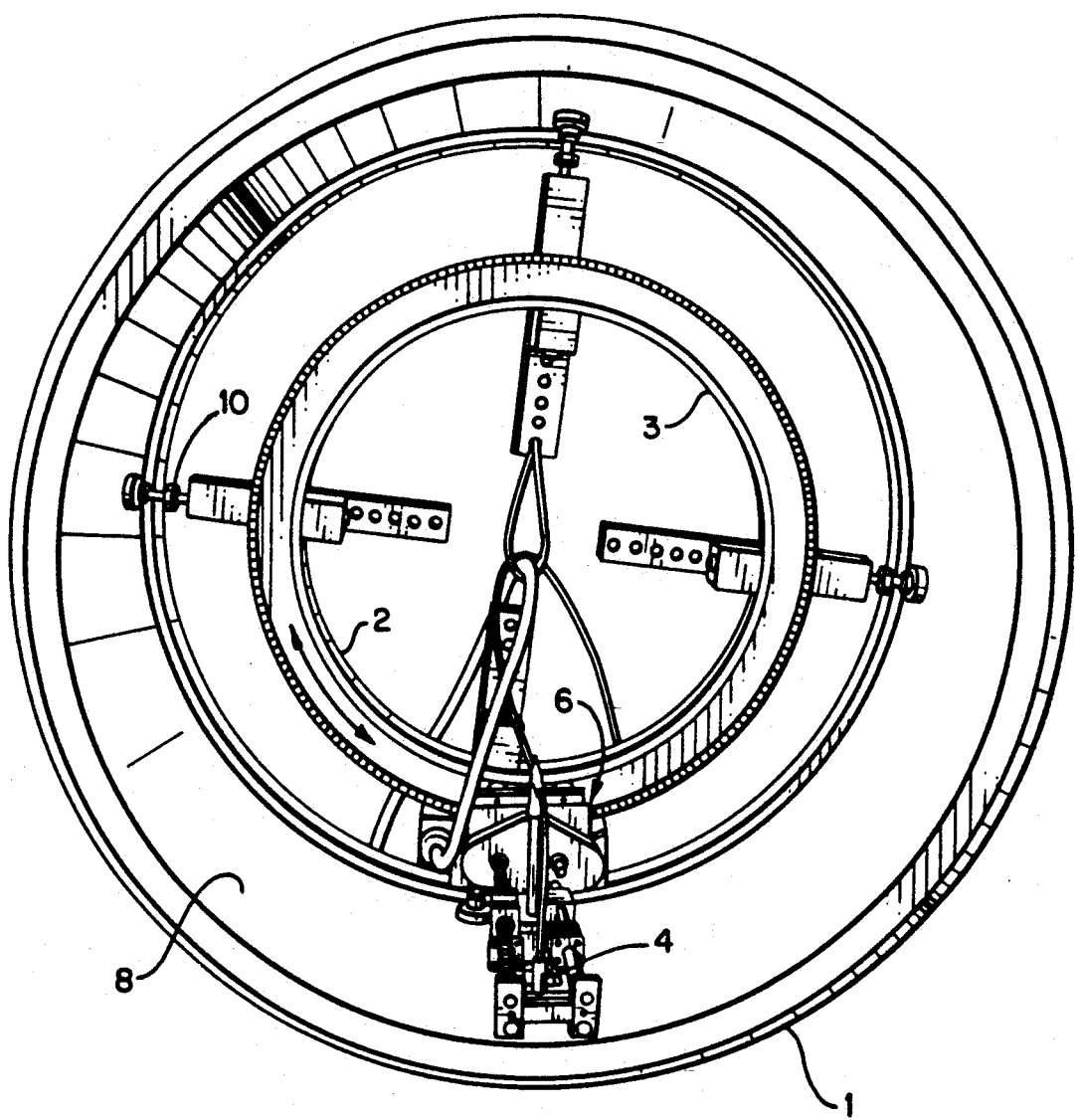
FIG. 1 is an end view of a generator retaining ring in which has been mounted a reference frame, a probe carriage and an eddy current probe.

FIG. 1 shows a retaining ring 1 for a large electric power generator (not shown) in which a reference frame 2 has been coaxially mounted. The retaining ring is substantially cylindrical and composed of a conductive metal in which eddy currents can be induced. The retaining rings are tightly fitted over the ends of rotors used in large power generators. Because these rotors operate at extremely-high rotational speeds, the retaining rings are subjected to large centrifugal forces. The retaining ring must be durable to withstand large centrifugal forces for long periods of time. Accordingly, the retaining ring must be substantially free of surface and sub-surface defects which could weaken the retaining ring and allow cracks to develop in the retaining rings. Centrifugal forces acting on the retaining ring could cause such cracks to propagate and lead to a catastrophic failure of the retaining ring.

Accordingly, the surfaces of the retaining ring are inspected for material flaws before being installed on generator rotors. This inspection is accomplished using eddy current probes 4 mounted in a carriage 6 that is movably fixed to the reference frame 2.

The eddy current probe traverses the entire surface 8 of the retaining ring in search for material flaws. The eddy current probe is slid axially across the retaining ring surface by the carriage and motorized reference frame. Each axial pass across the retaining ring surface is one straight scan line of the probe. After each scan, the carriage is indexed slightly around the circumference of the interior surface (in the direction theta $\theta$) of the retaining ring to position the eddy current probe on another scan line. The sequence of scanning the eddy current probe axially along the retaining ring surface and indexing the carriage with respect to the reference frame is repeated until the probe has traversed the entire circumferential surface of the retaining ring. Both the interior and exterior surface of the retaining ring may be inspected by the eddy current probe in this way.

The reference frame 2 is coaxially aligned with the retaining ring. In the preferred embodiment, the reference frame and a motorized Alara TM scanner mount 20 are conventional and manufactured by the Virginia Corporation of Richmond, Richmond, Va. The annular portion of the reference frame 3 is centered about the axis of the retaining ring by four orthogonal adjustment feet 10. These feet are adjusted in length to position the annular ring on the apparent axis of the retaining ring. (The ring is not precisely cylindrical and does not have a true axis.) The adjustment feet 10 have several holes on which the annular ring can be mounted. These holes accommodate the different radial sizes of annular frames needed for the various sizes of retaining rings.

The annular ring of the reference frame has an annular array of teeth that engage a motorized mount 20 as it moves around the annular frame. The engagement of the mount and the teeth allow the mount to be precisely indexed around the annular ring such that the annular position of the mount (and the probe) in the retaining ring can be controlled and determined.

Figure 2:
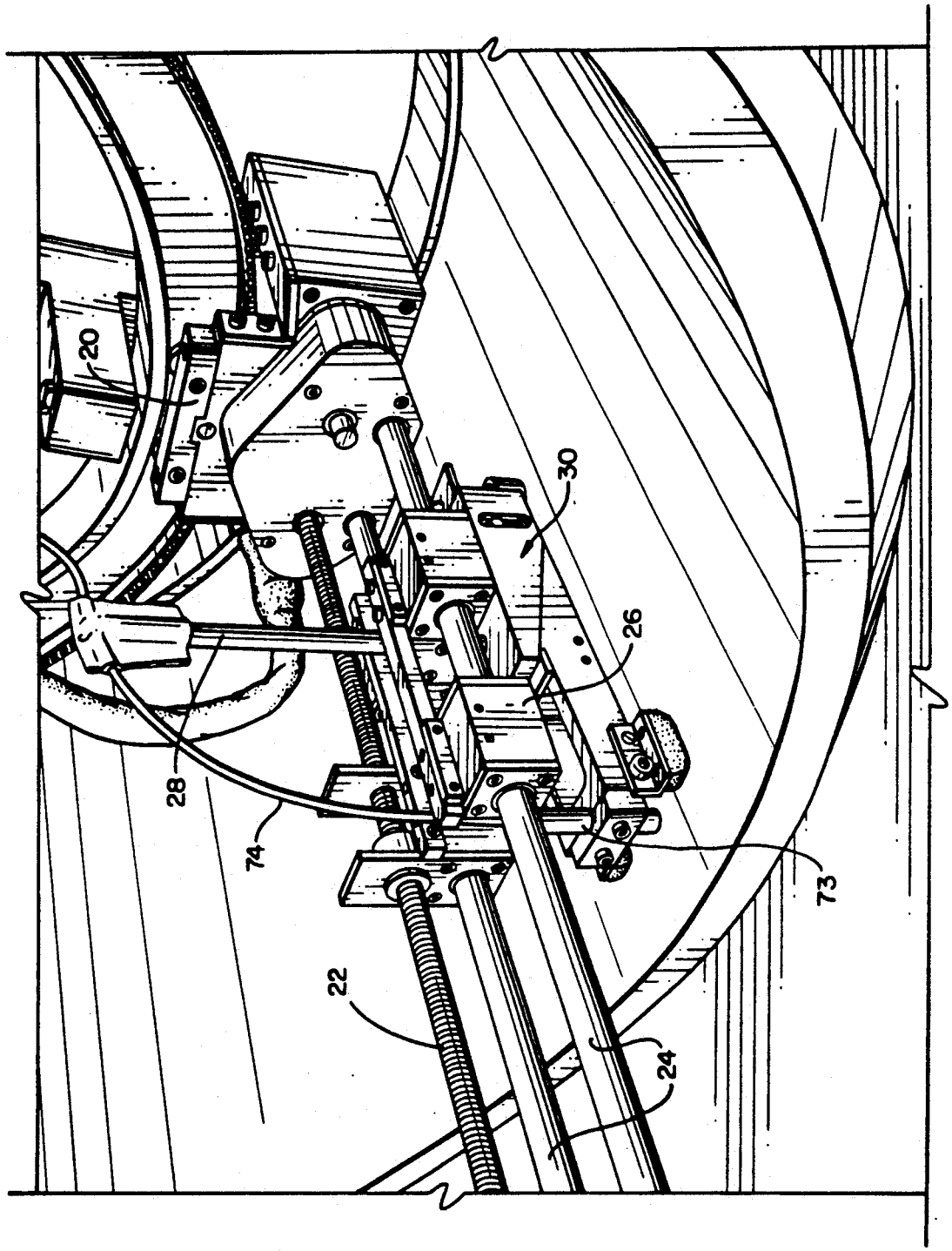
FIG. 2 is a perspective view of a probe and carriage mounted on a reference frame in a retaining ring.

As shown in FIG. 2, the mount includes three shafts that extend above the surface of the retaining ring and are parallel to the ring axis. The first shaft 22 is a threaded shaft that is rotated by the motorized mount. As the threaded shaft rotates it engages a mount bracket 26 and thereby moves the bracket and carriage 30 across the surface of the retaining ring. The other two shafts 24 maintain the alignment of the bracket and carriage. The bracket 26 slides along these parallel alignment shafts in a straight line parallel to the ring axis. The bracket 26 engages a rod 28 which is attached to the probe carriage 30 with screw 27. This rod couples the bracket 26 to the carriage. The movement of the bracket is translated to the carriage by the rod 28. The eddy current probe 73 is firmly held by the carriage and the probe is electrically coupled by a cable 74 to the signal processing electronics.

Figure 3:
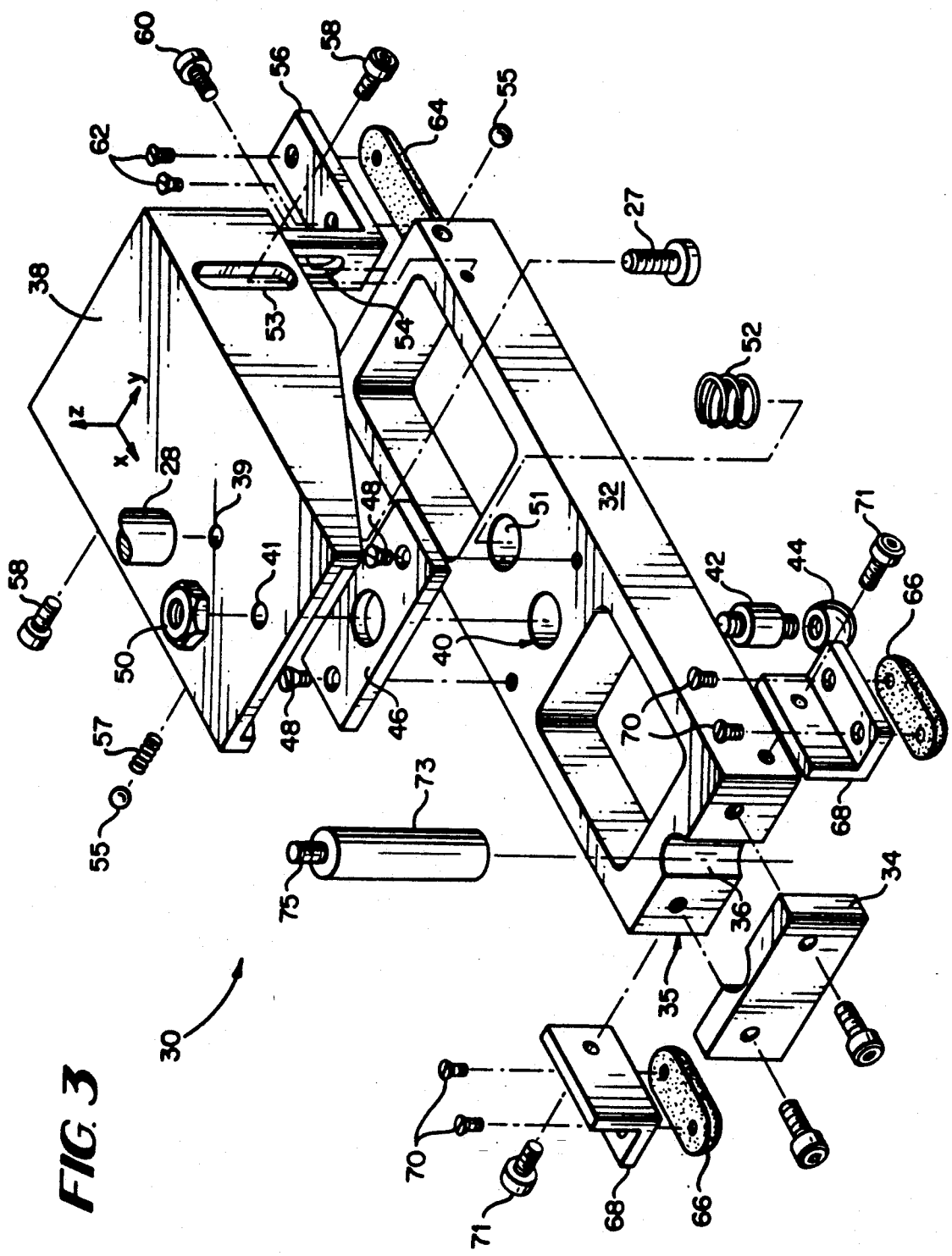
FIG. 3 is an exploded diagram of a probe carriage.

FIG. 3 shows the carriage 30. The carriage comprises a main body 32, a probe bracket 34 that holds the eddy current probe in slot 36 (if multiple probes are used, then multiple slots are provided on the noses of the carriage body) and a carriage plate 38 that is held firmly against the bottom of the mount bracket 26. Rod 28 is inserted perpendicularly into the carriage through hole 39 in the carriage plate 38 and is held in the plate by screw 27.

The translation movement of the rod 28 is transferred to the carriage via the carriage plate. The plate has three sides that loosely fit over the sides and back of the body. A threaded transition shaft 42 is attached to the carriage plate via nut 50. The transition shaft extends from the plate into a hole 40 in the carriage body. A spherical contact ball 44 is attached to the end of the threaded shaft 42. It is this contact ball that is in direct contact with the surface of hole 40 in the carriage body and transfers the force from the carriage plate to the carriage body. The contact ball 44 allows the carriage plate to move slightly (in the Z-axis) with respect to the body 32 without breaking contact between the ball and the body. Since the body of the carriage rides on the non-uniform surfaces of retaining rings, there will be relative movement between the body and the carriage plate. The spherical ball 44 allows the carriage body to move with respect to the plate without losing contact between the plate and the carriage body.

The amount of movement between the plate and the carriage body in the direction normal (Z-direction) to the carriage body and plate is limited by virtue of the ability of the ball 44 to slide up and down within hole 40. The ball and rod cannot slide out of the carriage body because shaft bracket 46 is attached by screws 48 to the top surface of the carriage body to prevent the shaft 42 from being pulled out of the carriage body.

Spring 52 between the carriage plate and body biases the carriage body away from the plate and against the surface of the material being tested. Spring 52 is positioned between the bottom of carriage plate 38 and the top surface of the carriage body. The top surface of the carriage body includes a shallow recess 51 in which sits the spring 52.

The carriage body 32 has limited degrees of freedom of movement with respect to the carriage plate 38 and hence the mount bracket. Referring to the XYZ coordinate shown for illustrative purposes on FIG. 3, the carriage plate allows displacement movement of the carriage body along the Z direction and rotational movement within the Y-Z plane (about the X axis). Movement in the Z direction is allowed by the operation of the slots 53 in the sides of the plate. Slot 53 in the carriage plate receives screw 58 that is threaded into the side of carriage body 32.

The limited rotational movement within the Y-Z plane is provided by the loose fit between the sides of the carriage plate and carriage body and by the loose fit between the screws 58 within slots 53. Pivot balls 55 between the sides of the carriage body and plate allow for the rotational movement. The pivot balls and spring 57 fit in the clearance between the sides of the carriage plate and of the body. The balls and spring allow the body to rotate but prevent the body from moving in the Y-direction with respect to the plate. The limited rotational movement along with movement along the Z axis allows the carriage body to ride along an uneven surface of the retaining ring while being pulled along by the rod 28.

The rotational movement and Z-displacement of the carriage body does not deflect the eddy current probe from a straight scan line along the X-direction. The carriage does not permit movement between the carriage plate and carriage in any direction which would cause the probe to move off a straight scan line. In FIG. 3, the X direction is the direction of movement of the probe and carriage and is parallel to the axis of the retaining ring. The X direction represents the scan line direction. Accordingly, the carriage moves in a straight line along the X direction. Movement in the Z direction between the carriage plate and the carriage body does not affect the straight line X direction movement of the probe. Similarly, limited rotational movement about the X axis does not cause the probe to veer off a straight scan path in the X direction. Accordingly, the ability of the carriage to move with respect to the carriage plate is restricted to those degrees of movement that do not affect the straight scan path of the probe.

The carriage body rides on feet 66 and 64. The feet slide along the surface of the retaining ring, and, in a preferred embodiment, are made of a self-lubricating elastic material such as Delrin ™ sold by the dupont corporation. The sliding foot 64 (secured by screws 62) is attached by bracket 56 and screw 60 in the carriage body. The sliding feet 66 are attached by brackets 68 and screws 70, 71 to the carriage body. The feet slide smoothly across the surface of the retaining ring without inducing vibration to the eddy current probe. As an alternative to sliding feet, rollers or caster feet have been found to be workable but to induce more mechanical noise in the probe signal than do the sliding feet of the preferred embodiment.

The distances between the three carriage feet ensure that the feet are close enough together so that irregularities in the surface shape of the retaining ring, e.g., out of roundness, do not cause variations in the lift-off gap between the probe and retaining ring surface. As the feet ride along the irregular surface of the retaining ring maintain a constant lift-off gap between the probe and the ring surface. However, the feet are far enough apart so that small defects or flaws in the retaining ring surface do not cause the movement of the carriage body to jolt or otherwise be abruptly changed.

The distance of the feet from the bottom of the carriage body is adjustable. The brackets 68 and 56 can be adjusted via slot 54 in bracket 56 so that the feet hold the carriage body level over the material surface being tested. Generally, the feet are adjusted each time the reference frame is set up in a retaining ring. The set up of the carriage is aided by the ability of the carriage body to be adjusted in the Z-direction with respect to the carriage plate and material surface.

The probe 73 is held in the bracket on the nose 35 of the carriage body. The preselected lift-off gap between the probe and ring surface (typically 0.002 in. ± 0.0005 in.) is initially set by Mylar shims inserted between the probe and ring surface while bracket 34 is attached to the carriage body. Once this bracket is firmly attached to the carriage body and probe, the Mylar shims are removed and the probe is held in place on the carriage body by bracket 34.

Figure 4:
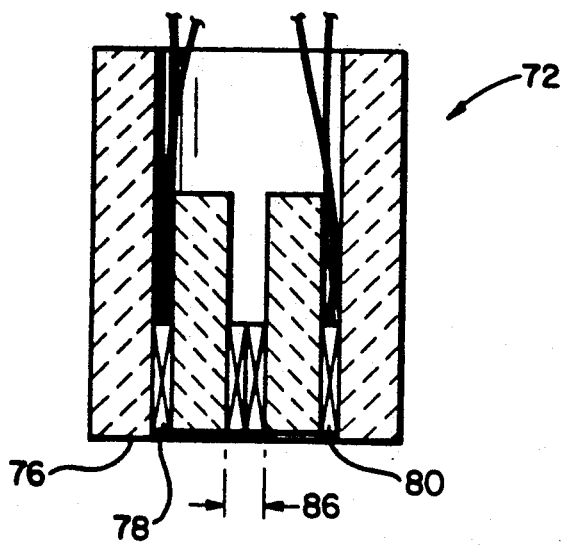
FIGS. 4 and 5 are orthogonal side views of a split core eddy current probe.
Figure 5:
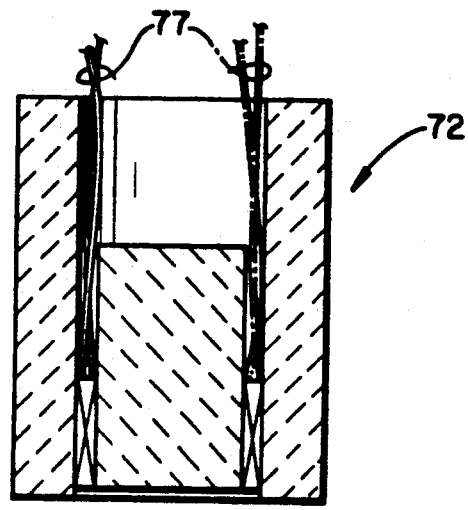
Figure 6:
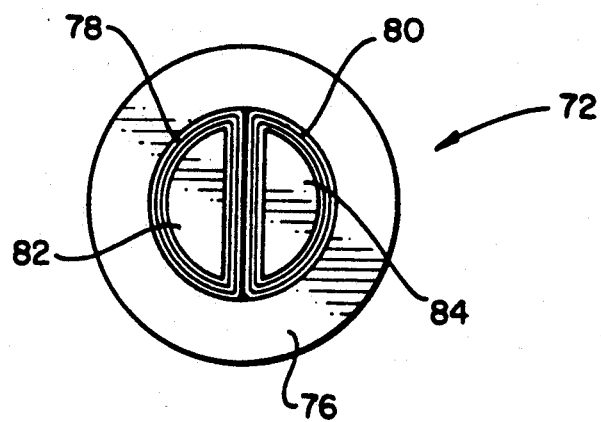
FIG. 6 is an end view of the face of the eddy current probe shown in FIGS. 4 and 5.

FIGS. 4, 5 and 6 show the active element 72 of the eddy current probe. Eddy current probe 73 is a hollow cylindrical tube of ferrite material having at one end a threaded adapter 75 for coupling the coil wires to an instrument cable 74. At the opposite end of the probe tube is an active element 72. A pair of signal wires from each coil is passed from the active element 72 through the interior of the eddy current probe and to the cable 74.

The active element 72 of the probe is a small hollow cylinder of a ferrite material such as a ceramic manganese, zinc and iron composition. The ferrite concentrates the magnetic field from the coil and directs the magnetic field towards the face 76 of the active element that is adjacent the retaining ring surface. In the interior of the ferrite cylinder are the two coils 78, 80 each surrounding one of the two split cores 82, 84. The split cores are formed of the same ferrite material as is the ferrite cylinder.

In the preferred embodiment, each copper wire coil has 54 turns around a ferrite split core 80, 82. The shape of the coil conforms to the shape of the "D" shaped split core. After being wound, each coil is covered with a double layer of installation (PB-1 insulation). The first insulation layer is nylon and the second layer is a polyvinyl alcohol. This second insulation layer is softened by wetting its surface with methanol or some other alcohol. After the alcohol used to soften the outer insulation layer dries, the wound coil is strong enough to be assembled into the ferrite cylindrical tube of the active element.

The split cores are each ferrite rods which, in the preferred embodiment, are formed from small ferrite rods split in half. To make the split cores, the ferrite rods are glued to a lapping plate using a solvent-removable glue. Lapping is a grinding operation for making the "D" shaped cross section from a round rod. The raw ferrite material is powder which is made into a slurry, and extruded through a die as a round rod. The height of the lapping plate from the lapping base plate is measured with a micrometer caliper to ensure that the proper dimensions of the ferrite rods are maintained. Lapping is performed with a closed silicon carbon paper. The lap rods are moved from the lap by washing away the removable cement.

During manufacture, the gap 76 between the split ferrite cores is maintained by Mylar shims between the two cores. This Mylar spacer is positioned at the end of the split cores away from the coils and the face of the active element. Once the coils have been wound around the split cores, and the coil and cores have been inserted in the hollow tube 72 of the active element, the Mylar shim is removed from between the split cores.

The coil and cores are inserted in the cylindrical tube 72 such that the axial position of the coils within the cylindrical body is slightly recessed from the front plane 76 of the axial body. In the hollow end of the cylindrical body behind the coil and split cores, the cylindrical body is filled with a cyanoacrylic glue that cements the windings, core, signal wires and cylindrical body together. Similarly, cyanoacrylic glue is also applied to the front face of the active element to secure the active element together and to fill in any gaps in the front face of the active element. The front face of active element is smooth to prevent dirt and other foreign objects from embedding in the front face of the active element.

Figure 7:
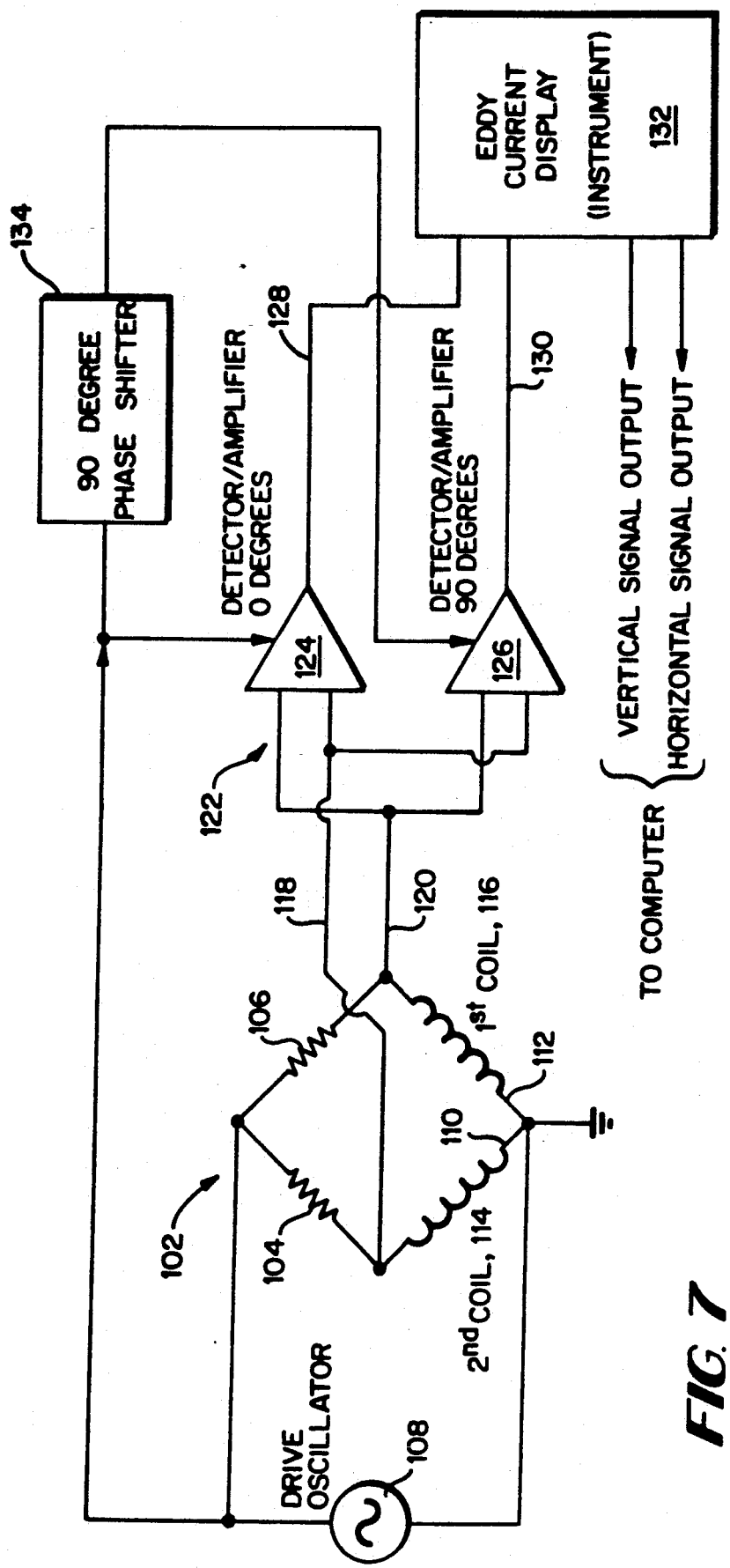
FIG. 7 is a schematic diagram of a balance bridge and differential circuits for processing probe signals.

FIG. 7 shows a schematic circuit diagram of the signal processor for the coil signals. Typically, this circuit, with the exception of the probe coils, is contained in an eddy current instrument. A signal cable from the probe coil is coupled to the instrument. The pair of wires 77 from each of the two split coils carried by the cable are coupled to a balanced impedance bridge circuit 102. Two of the arms 104, 106 of this bridge circuit have identical electrical resistance values and are coupled to a drive oscillator 108 that provides the alternating high frequency current for the coils. The other two arms 110 and 112 are coupled to the eddy probe coils 114 and 116. The coils are grounded within the bridge. Accordingly, both coils receive identical oscillating currents through the bridge.

The bridge is used to detect impedance imbalances between the two coils. Current signals from the coils are passed through the leads 118 and 120 that couple the bridge circuit to the signal processing portion 122 of the circuit. The signal processing portion includes two detectors/amplifiers 124, 126. These detector/amplifiers compare the impedance between the two coils and provide difference signals over leads 128, 130. These differential amplifiers 124, 126 are coupled to both the coils. The first detector/amplifier 124 is synchronized with the drive oscillator such that it compares both of the coil signals in phase. The difference signal generated by this detector/amplifier reflects the in-phase impedance differences between the two coil current signals. This in-phase difference signal is provided to an eddy current display device 132. Similarly, the second detector/amplifier 126 compares the two coil current signals. However, this detector/amplifier compares the out-of-phase impedance components of the current signals. A 90° phase shifter 134 coupled to the drive oscillator imposes a 90° phase shift to this detector/amplifier 126. This detector/amplifier generates a difference signal over line 130 which reflects the out-of-phase differences between the current signals in the two coils. This out-of-phase difference signal is also provided to the eddy current display 132.

The eddy current display is a conventional device used to display eddy current probe data usually by means of an oscilloscope type display. It can be coupled to a strip chart or a computer controlled a CRT display or other color printout. The computer may be used to analyze the data from the eddy current probe.

While the invention has been described in its preferred embodiment, the invention is not limited to this disclosed embodiment. Rather, the invention covers various modifications and equivalent arrangements included within the spirit and scope of the appended claims.

What is claimed is:

1. An apparatus for monitoring eddy currents comprising:

an eddy current probe having at least one current carrying coil;

a carriage body on which said probe is mounted and in slidable contact with a surface of a stationary cylindrical body such that said probe is held a constant distance from said surface;

a translation means for moving said carriage body and eddy current probe along a scan line across said surface, said scan line being parallel to the axis of said cylindrical body, and coupling means for coupling said carriage to said translation means for moving said carriage and said probe along a predetermined probe path parallel to said axis, wherein said coupling means allows relative movement between said carriage and translation means such that said probe does not veer from said predetermined scan line, said coupling means comprising a carriage plate fixed to said translation means, and slidably and pivotably contacting said carriage body, wherein said carriage plate having relative movement with respect to said carriage body and said carriage plate includes bracketing side panels having slots or post slidably engaging posts or slots on at least two sides of said carriage body.

2. An apparatus for monitoring eddy currents comprising:

an eddy current probe having at least one current carrying coil;

a carriage body on which said probe is mounted and in slidable contact with a surface of a stationary cylindrical body such that said probe is held a constant distance from said surface;

a translation means for moving said carriage body and eddy current probe in a scan line direction parallel to the axis of said cylindrical body, and coupling means for coupling said carriage to said translation means for moving said carriage and said probe along a predetermined probe path parallel to said axis, wherein said coupling means allows relative movement between said carriage and translation means such that said probe does not veer from said predetermined scan line path, said coupling means comprising a carriage plate fixed to said translation means, and slidably and privotably contacting said carriage body;

said carriage plate having relative movement with respect to said carriage body and said carriage plate includes bracketing side panels having slots or posts slidably engaging posts or slots on at least two sides of said carriage body, said carriage plate is coupled to said carriage body via a contact ball attached to said carriage plate, said contact ball being in slidable and pivotable engagement with a hole in said carriage body, wherein a shaft bracket attached to the carriage body confines said contact ball within said hole.

3. An apparatus comprising:

an eddy current probe having an inductance coil oriented with an axis substantially perpendicular to an interior surface of a hollow metallic cylinder;

an eddy current probe bracket holding said probe;

a carriage body attached to said probe bracket and probe, comprising feet slidably engaging said surface and supporting said probe a constant distance above said surface;

a carriage plate having a slot or post slidably engaging a post or slot on said carriage body to provide relative movement between said body and plate in a direction parallel to said axis of the coil, and to provide limited rotational movement between said body and plate about an axis orthogonal to said axis of the coil;

a mount bracket fixed to said carriage plate comprising translation means for moving along a straight scan line path parallel to the axis of said cylinder, and a contact ball attached to said carriage plate and slidably engaging said carriage body such that said carriage body and probe move in a straight path parallel to said straight path of said mount bracket.

4. An apparatus as in claim 3 further comprising a spring between said carriage plate and said carriage body, said spring exerting a biasing force against said body and towards said surface.

5. An apparatus as in claim 3 further comprising pivot balls between said carriage plate and carriage body.

* * * * *